(12) United States Patent
Trochesset (10) Patent No.: US 6,227,034 B1
(45) Date of Patent: May 8, 2001

(54) INTEGRATED VALVE DESIGN FOR GAS CHROMATOGRAPH

(75) Inventor: Wallace Trochesset, Friendswood, TX (US)

(73) Assignee: Daniel Industries, Inc., Houston, TX (US)

( * ) Notice: Subject to any disclaimer, the term of this patent is extended or adjusted under 35 U.S.C. 154(b) by 0 days.

(21) Appl. No.: 09/174,203

(22) Filed: Oct. 16, 1998

(51) Int. Cl.[7] ............................. G01N 30/04; G01N 1/22
(52) U.S. Cl. ................. 73/23.42; 73/61.56; 73/53.01; 422/89; 422/93
(58) Field of Search .................. 73/53.01, 23.35, 73/23.42, 61.56, 61.57, 61.59, 61.73; 422/83, 89, 93

(56) References Cited

U.S. PATENT DOCUMENTS

| | | | |
|---|---|---|---|
| 3,095,746 | * | 7/1963 | Reinecke et al. ................ 73/422 |
| 3,139,755 | * | 7/1964 | Reinecke et al. ................ 73/422 |
| 3,203,249 | * | 8/1965 | Tentzsch et al. ................ 73/422 |
| 3,386,472 | * | 6/1968 | Szonntagh ..................... 137/597 |
| 3,393,551 | * | 7/1968 | Todd et al. ..................... 73/23.1 |
| 3,627,992 | * | 12/1971 | Davies et al. ............. 235/61.11 J |
| 3,916,465 | * | 11/1975 | Jones ............................ 73/23.1 |
| 3,975,946 | * | 8/1976 | Ball et al. ....................... 73/61.1 |
| 4,958,553 | * | 9/1990 | Ueno ............................. 91/447 |
| 5,099,884 | * | 3/1992 | Monahan ....................... 137/827 |
| 5,567,868 | * | 10/1996 | Craig et al. .................... 73/23.42 |
| 5,581,028 | * | 12/1996 | Barth et al. ................... 73/204.26 |
| 5,767,387 | * | 6/1998 | Wang .......................... 73/23.42 |

* cited by examiner

Primary Examiner—Hezron Williams
Assistant Examiner—David J. Wiggins
(74) Attorney, Agent, or Firm—Conley, Rose & Tayon, P.C.

(57) ABSTRACT

A gas chromatograph with multiple valves is disclosed. An embodiment of the multi-valve gas chromatograph includes multiple valves and multiple thermal conductivity detectors (TCD's). This allows separation and measurement of a gas sample in one compact integrated unit.

Other features may also be present. For example, a first heating zone may include a band heater placed around the multi-valve block to heat the carrier gas and to keep the multi-valve block at a desired temperature. A second heating zone may include a spool and a cartridge heater to heat the columns through which the gas sample flows. Two sets of screws, one through the top of the multi-valve and one through the bottom, may be included to simplify maintenance of the multi-valve system. Insulation defining an oven can be placed around the assembly to stabilize the temperature of the multi-valve assembly.

2 Claims, 13 Drawing Sheets

FIG. 3B (OFF)

INTEGRATED VALVE DESIGN FOR GAS CHROMATOGRAPH

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

This invention relates to the field of gas chromatography. In particular, this invention relates to a new gas chromatograph. Even more particularly, this invention relates to a new gas chromatograph having multiple valves and detectors.

2. Description of the Related Art

The field of gas chromatography is concerned with analyzing gas samples flowing through a process pipeline. A sample is provided to a gas chromatograph, which then separates the sample into portions and uses a variety of detectors to analyze the concentration of particular components in the process stream.

Before now, a number of problems have existed with gas chromatographs. For example, fast and accurate measurements are desirable for any gas chromatograph. A gas stream flowing through the process pipeline may be composed of many different classes of components and ideally, each of these components would be analyzed. However, conventional gas chromatographs cannot respond to process changes as quickly as desired. Further, liquid contaminants in the process stream can introduce further complications to any analysis.

Another problem with previous gas chromatographs is a lack of flexibility in analysis of the gas stream. It would often be desirable to analyze different characteristics of the gas stream without switching to another gas chromatograph. However, previous gas chromatographs are restricted because of their limited number of valves and their lack of flexibility. As such, a gas chromatograph is needed that can analyze complex process streams with greater accuracy and speed.

Other problems with gas chromatographs have also existed in the valve system contained in gas chromatographs. For example, these valves are not easy to service. Maintenance may be necessary because often the flows through a gas chromatograph are dirty, and this contamination can affect the performance of key components in the gas chromatograph. Substitution of clean components in the gas chromatograph can minimize the problem, but disassembling the gas chromatograph has in the past been a difficult and frustrating experience. Thus, a need for a new gas chromatograph exists.

As known by those of ordinary skill, the prior art also presents other problems that should be solved or minimized.

SUMMARY OF THE INVENTION

A disclosed embodiment of the invention is a multi-valve assembly including a plurality of plates and diaphragms attached together to form multiple valves. Each of these valves is individually actuatable by an outside source and includes a plurality of valve ports. The assembly may also include a reception area where at least one fluid properly detector, such as a TCD, may be inserted. The assembly preferably includes an open area in the body of plate that holds a spool. The spool includes a heater and heats a gas sample to a predetermined temperature while the remainder of the plates heat carrier gas to a second predetermined temperature by use of a band heater.

The disclosed embodiment also includes two sets of screws, a first set attaching a top plate of the invention to at least one middle plate, and a second set attaching a bottom plate of the invention to at least one middle plate, the top plate being removable without the bottom plate becoming detached.

The invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made accompanying drawings, wherein.

DETAILED DESCRIPTION OF THE PREFERRED EMBODIMENT

Figure 1:
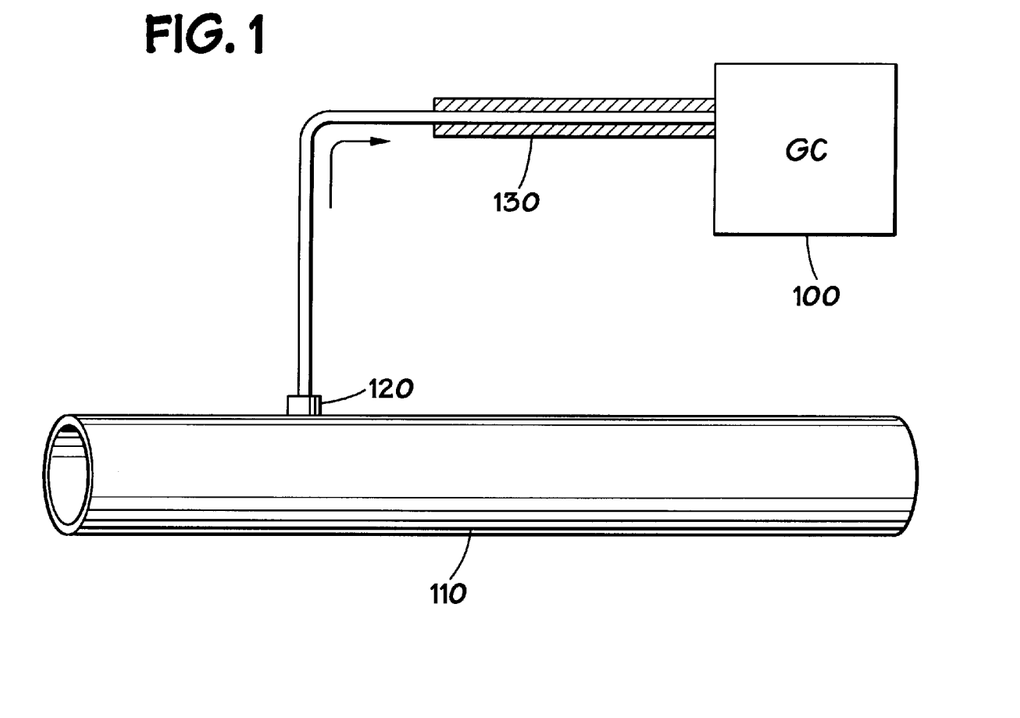
FIG. 1 is a simplified diagram of a gas chromatograph system.

FIG. 1 shows a gas chromatograph system generally built in accordance with the teachings herein. Gas flows through a process pipeline 110, a sample of which is taken by a sample probe 120 prior to being introduced to gas chromatograph (GC) 100. The gas sample may be filtered and heat traced generally along tubing 130 before flowing into gas chromatograph 100. This heating may be required for gases that may condense into a part gas, part liquid flow at cooler temperatures. After being analyzed by the gas chromatograph, the gas sample is either returned into the process pipeline 110, or vented to the atmosphere.

Figure 2:
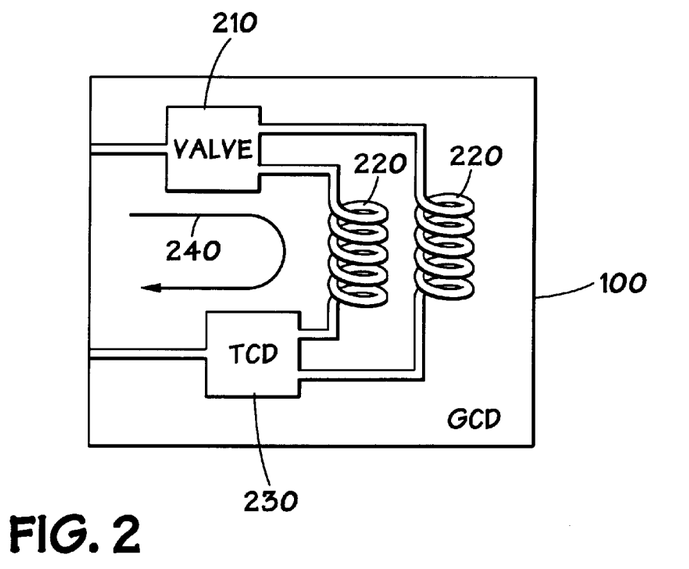
FIG. 2 is a simplified schematic of a gas chromatograph.

Referring to FIG. 2, gas chromatograph 100 includes valve assembly 210 connected to multiple columns 220 and detectors 230, in this case, thermal conductivity detectors (TCD). A gas sample generally follows path 240 through valve assembly 210, columns 220 and TCDs 230. The valve assembly allows the selection of columns 220 which contain a liquid phase, or porous polymer, or other material that acts to separate the gas sample into multiple portions, each portion being sequentially released to the TCDs 230. For example, a gas sample may contain various molecular weight hydrocarbon components. Column 220 could separate the gas sample so that lower molecular weight hydrocarbon components would elute from the column first, followed by a higher molecular weight component, etc.

Figure 3A:
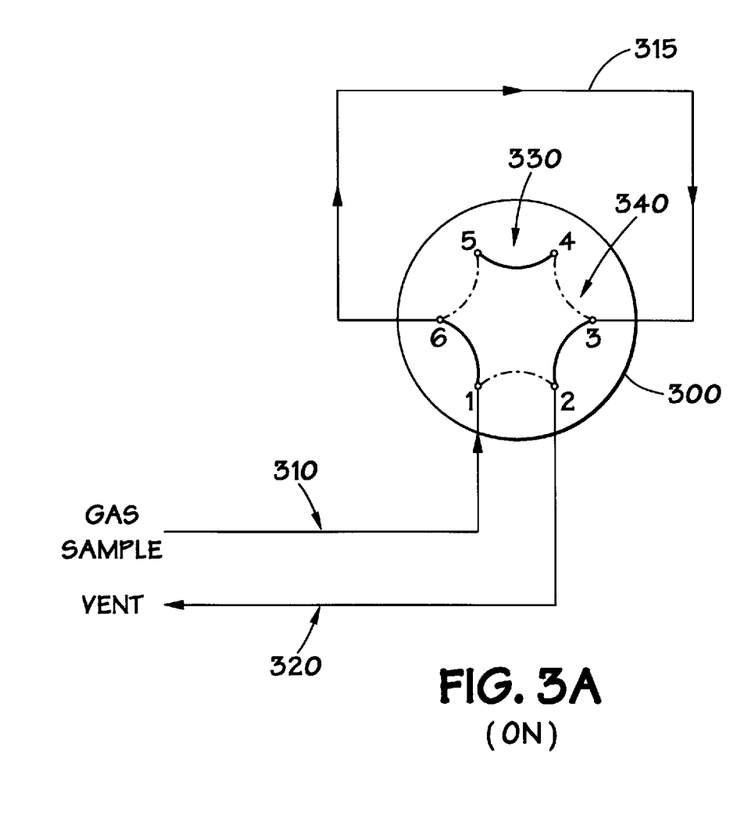
FIG. 3A is a schematic diagram of a valve in an ON configuration.
Figure 3B:
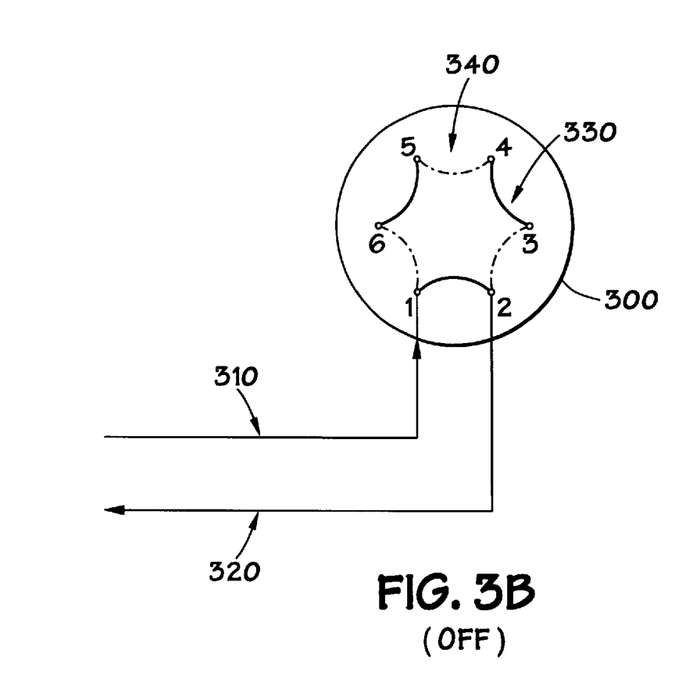
FIG. 3B is a schematic diagram of a valve in an OFF configuration.

Referring to FIGS. 3A and 3B, the operation of a valve is shown. Valve 300 includes a plurality of valve ports, labeled 1–6. It will be appreciated that more or fewer number of ports may also be used. Incoming line 310 provides a gas sample to valve 300. Exhaust line 320 expels the gas sample from the valve 300. Solid lines 330 show open passages between ports, whereas dotted lines 340 indicate blocked passages between the ports.

A solenoid (not shown) places valve 300 into either an ON position, as shown in FIG. 3A, or an OFF position, as shown in FIG. 3B. When a valve is in the ON position, gas flows from incoming line 310, through port 1 to port 6, through line 315 and finally through port 3 to port 2 and out exhaust line 320. When the valve is in the OFF position, gas flows from incoming line 310, through port 1 to port 2 and out through exhaust line 320.

Figure 3C:
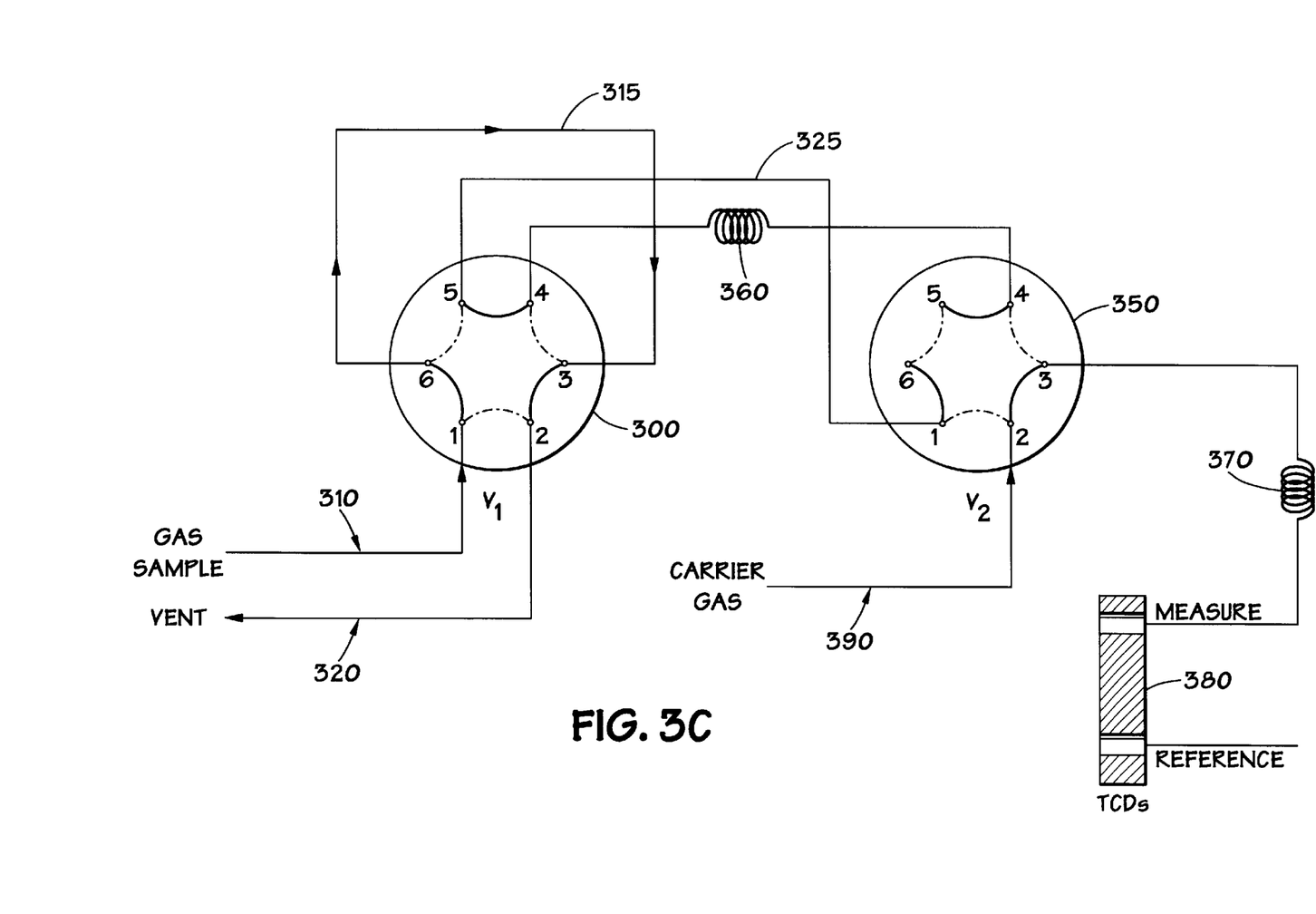
FIG. 3C is a schematic diagram of a multiple valve system for analyzing a sample.

FIGS. 3C and 3D illustrate how a pair of valves may operate either alone or in combination with additional valves (not shown). A first valve 300 includes an array of 6 valve ports. A second valve 350 also includes an array of 6 valve ports. Associated tubing 310, 315, 320, 325 and 390, and columns 360 and 370 are also shown as well as dual TCD 380.

Incoming line 310 is attached to a sample transport line (not shown). When first valve 300 in an OFF position, gas sample flows from incoming line 310 to port 1 to port 2 of the valve 300 and out exhaust line 320. When valve 300 is in an ON position, however, gas sample flows from port 1 to port 6 and then through sample loop 315. That gas then flows from port 3 to port 2 of valve 300 and is expelled out exhaust line 320. At this time, the sample loop 315 is filled with a gas sample. This means that, if valve 300 is turned OFF at this time, a gas sample is trapped within the sample loop 315.

Turning now to valve 350, when it is in an OFF configuration, carrier gas flows from carrier gas input line 390 through port 2 of valve 350, to port 1 and then through carrier tubing 325. At this time, valve 300 is also in an OFF configuration, so that the carrier gas in tubing 325 is forced through port 5 to port 6 and through gas sample tubing 315. Consequently, this action forces the gas sample down column 360 via ports 3 and 4. The gas sample can then additionally be forced through column 370 and into the dual TCD 380 via ports 4 and 3. Many other port combinations also exist and are within the skill of one in the art. Thus, the valves may be connected in series to form "channels."

Each channel feeds into a corresponding TCD pair (a measurement TCD and a reference TCD). Use of more than one TCD pair results in a simultaneous analysis by the TCD's of the sample flowing through their corresponding attached columns. This parallel analysis results in a increased analysis speed as compared to serial analysis. Further, because technology currently limits the channels and the detector pairs to a one-to-one correspondence, the number of channels in use at any particular time is limited both by the number of valves and by the number of detectors. Of course, the greater the number of valves, the greater the number of potential channels, and the more potential for more parallel processing and a faster overall system. But even if the number of detectors limits the number of channels being used at any one time, a greater number of valves results in a greater number of channels from which to choose for each TCD. For example, a multi-valve system may have sufficient valves to operate eight channels. Even if only two detector pairs exist, such that only two channels can be in use at any one time, the detector pairs can be designed to select which channel among those eight channels it is connected to. This dramatically increases the flexibility of the presently disclosed gas chromatograph system.

Figure 4:
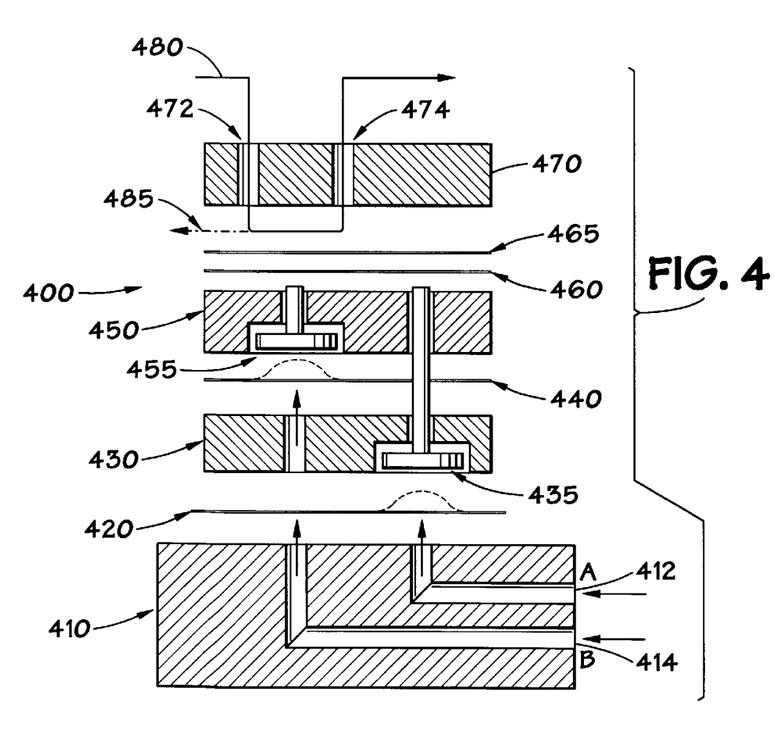
FIG. 4 is an illustrative cut-away view of a valve.

Referring to FIG. 4, a cross-section of a partial valve assembly is shown. Valve 400 includes a base plate 410 with activation ports 412 and 414, a lower actuator diaphragm 420, a lower piston plate 430 with associated long piston 435, upper actuator diaphragm 440, upper piston plate 450 with associated short piston 455, cushion diaphragm 460, sealing diaphragm 465, and primary plate 470 with valve ports 472 and 474 therein. These valve ports suitably could be ports 1 and 6 as shown in FIG. 3.

Referring back to FIG. 4, gas sample 480 enters valve port 472. This gas sample 480 travels out valve port 474 when long piston 435 is in an elevated (closed) position and short piston 455 is not. Long piston 435 is elevated by gas pressure applied to activation port A 412. This pressure deforms lower actuator diaphragm 420 and forces long piston 435 in an upward direction in lower piston plate 430. Upper end of long piston 435 then abuts against primary plate 470. Similarly, short piston 455 is actuated by gas pressure from activation port B 414, and forces gas sample 480 to path 485.

Figure 5:
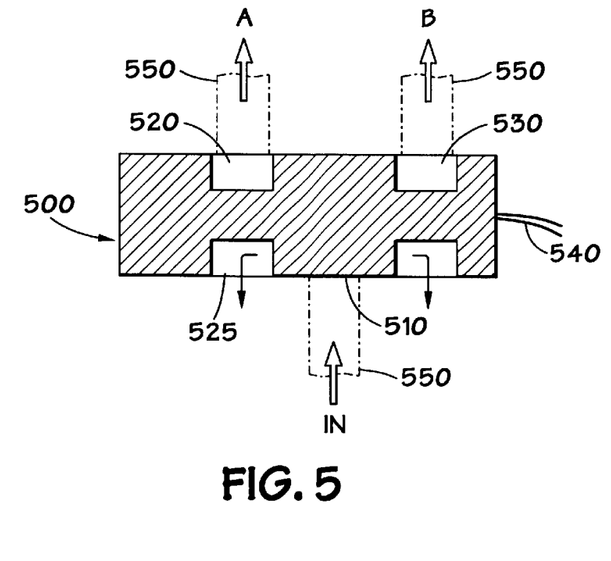
FIG. 5 is an illustrative cut-away view of a solenoid.

Whether a valve is in an ON or OFF position depends upon a solenoid that applied gas pressure alternately to either activation port A or activation port B. FIG. 5 generally illustrates the operation of a solenoid. Solenoid 500 includes a common line port 510, exit port 520 corresponding to activation port A, exit port 530 corresponding to activation port B, release port 525 for exit port A or exit port B, and control leads 540. Tubing 550 connects to each of common line port 510, and exit ports 520 and 530. Exit ports A and B connect to activation ports A and B in FIG. 4, respectively. Common line port 510 connects to a gas under pressure. Gas pressure applied to either of activation port A or activation port B controls whether the corresponding valve is in an ON or OFF position. Electrical control signals from leads 540 control whether common line 510 is connected to exit port A or exit port B, and thus whether gas pressure is applied to activation port A or activation port B. Some variation to the particulars of this design is possible while still staying within the teachings of the invention.

Figure 6:
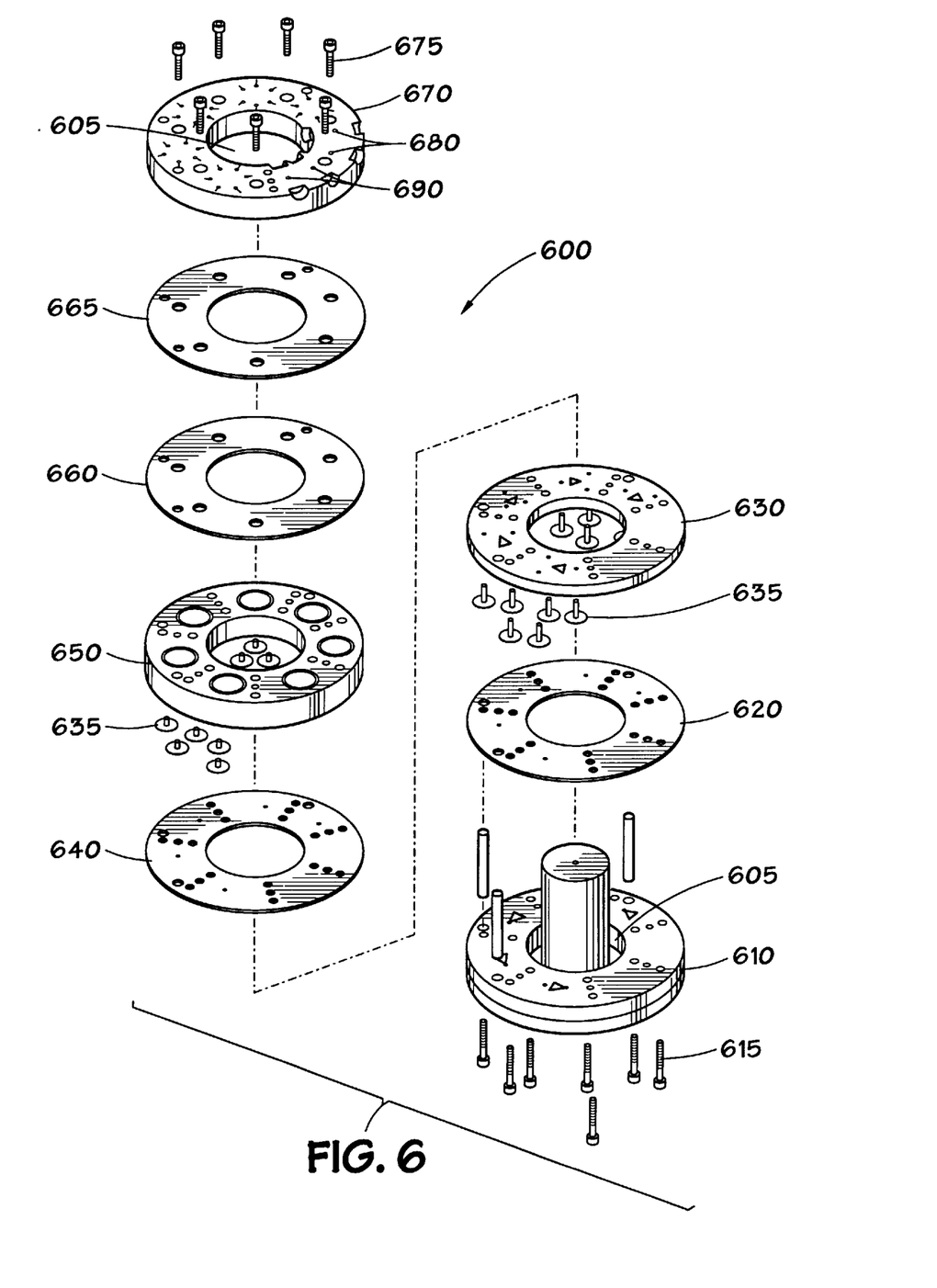
FIG. 6 is an exploded isometric view of an embodiment of a multi-valve block.

FIG. 6 shows an exploded view of an embodiment of the multi-valve block 600 including an open area 605, base plate 610 with associated dowel pins to align components, a lower activator diaphragm 620, a lower piston plate 630 with associated long pistons 635, an upper activator diaphragm 640, an upper piston plate 650 with associated short pistons 655, a cushion diaphragm 660, a sealing diaphragm 665, and a primary plate 670. Each piston includes a lower base portion with a pole extending therefrom. Hole sets 680 and 690 are suitable for two pairs of TCD's. First set of screws 615 for insertion through base plate 610, lower piston plate, and upper piston plate are shown as well as a second set of screws 675 for insertion through primary plate 670, upper piston plate 650, lower piston plate 630, and base plate 610. In addition, because there are five valves, five solenoids (not shown) are also present, each controlling a different valve.

As can be seen, the multi-valve device 600 includes 5 valves, with each valve having six ports. By integrating multiple valves into a single multi-valve block, a compact device is achieved that can separate a gas sample into a large number of columns as discussed above. This facilitates faster and more precise analysis of the gases contained in the gas sample. Manufacturing costs can also be reduced. The teachings herein can be used to integrate more or fewer than 5 valves into a single unit, and more or fewer valve ports per valve. For example, if a greater number of valves is desired, up to 7 valves can easily be located in the embodiment shown in FIG. 6.

One manner in which the embodiment of FIG. 6 makes faster and more precise analysis of the gas sample is reduction of what is known as "dead volume." Increased dead volume results when the components of a gas chromatograph are widely spaced and undue mixing of the fluid occurs. This mixing of the gas or fluid sample results in a "band broadening." Band broadening is undesirable because the area of each band of an analysis corresponds to a concentration measurement and these bands should not overlap. Consequently, a series of broad bands results in a much slower analysis than is possible with a series of short bands. Therefore, an integrated, compact design is particularly desirable from a performance perspective. Further, the illustrated geometry provides sufficient area for a first and second set of TCD's. While these TCD's may be located outside the multi-valve block if desired (e.g. to integrate a greater number of valves into the multi-valve block), the inclusion of the TCD's in the multi-valve block helps further miniaturize the device and make it more compact.

Figure 7A:
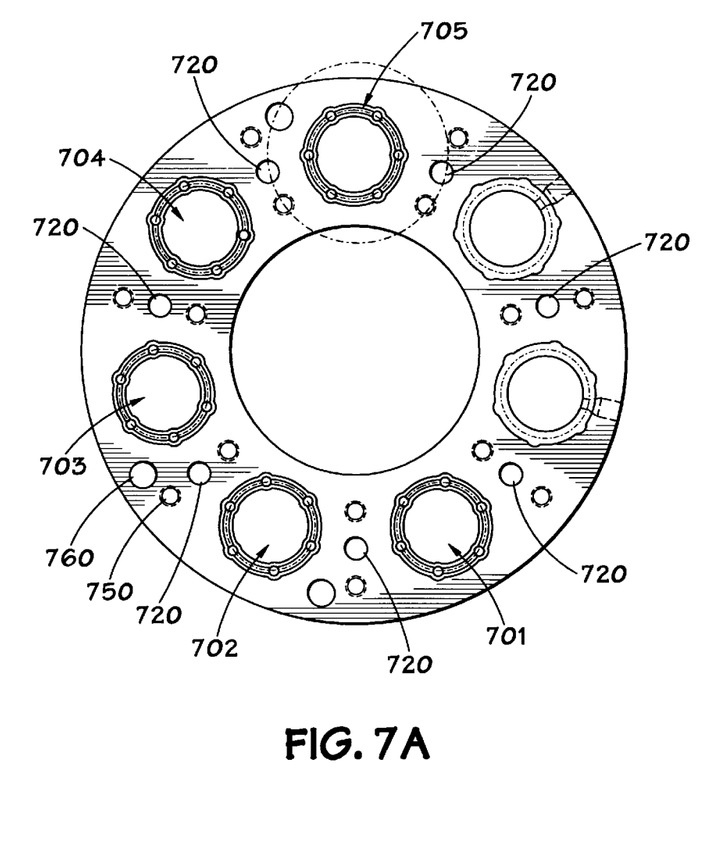
FIG. 7A is a top view of an upper piston plate for the multi-valve block of FIG. 6.
Figure 7B:
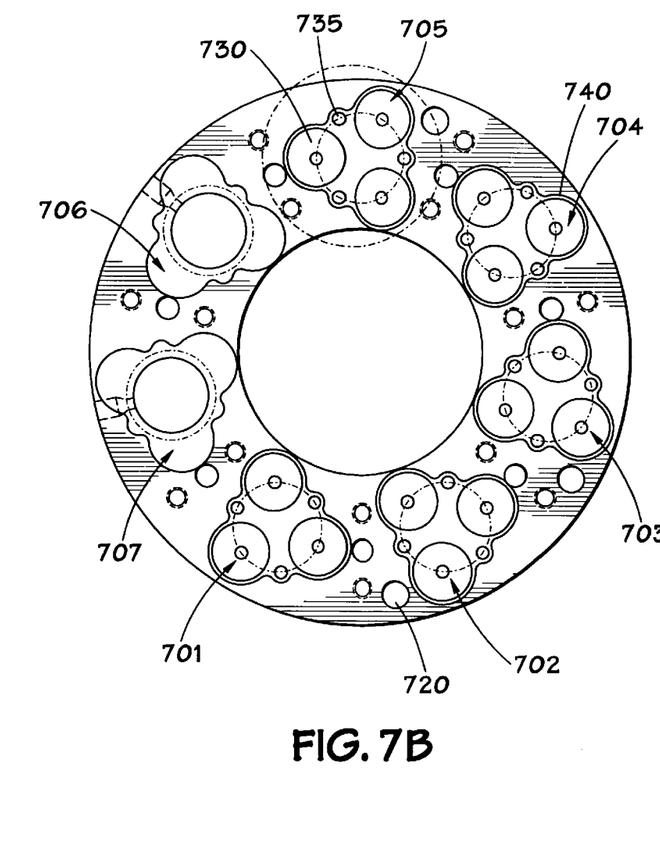
FIG. 7B is a bottom view of an upper piston plate for the multi-valve block of FIG. 6.

FIGS. 7A and 7B show top and bottom views respectively of the upper piston plate of FIG. 6. Referring to the top view of FIG. 7A, locations 701–705 for 5 valves are shown. Screw holes, generally at 720, are also shown for accepting screws to tighten together the primary plate with other plates. Holes 750 are for screws from the bottom to tighten the plates together, while holes 760 are for dowel pins to position the valves. Turning to the bottom view of the upper piston plate shown in FIG. 7B, locations 701–707 are similarly shown. Each valve includes sufficient room 730, 735 for 3 piston bases and 3 piston poles. Raised edges 740 around the perimeter of each valve location are also shown. The raised surfaces defined by the raised edges exist on both sides of the upper and lower piston plates. A raised edge of 0.032 inches could be used, for example. These raised edges 740 reduce the surface area upon which the screws 615 and 675 provide force and thereby reduce the chance of leakage.

Referring back to FIG. 6, it can be seen that two sets of screws are shown corresponding to holes 720 and 750. These two sets of screws that protrude through holes 720 and 750 simplify maintenance of the invention. A bottom set of screws 615 extends through the base plate 610, lower piston plate 630, and upper piston plate 650. Screws 615 attach these plates together. A top set of screws 675 extends through the primary plate, the upper piston plate, and the base plate to hold those plates together. This dual screw set approach simplifies maintenance because the loosening and removal of screws 675 allows access and replacement of the sealing diaphragm 665 and cushion diaphragm 660 without disassembly of a greater number of plates than necessary. It is the sealing diaphragm that becomes most contaminated by the dirty gas that flows through the multi-valve. A relatively low torque of about 10 ft/lbs. has been found acceptable for these screw sets while making the removal of these screws as easy as possible. The multi-valve configuration also simplifies maintenance because, by virtue of multiple valves in an integrated unit, replacement of only one diaphragm is necessary rather than the multiple diaphragms that would otherwise be necessary for multiple valves.

Figure 8A:
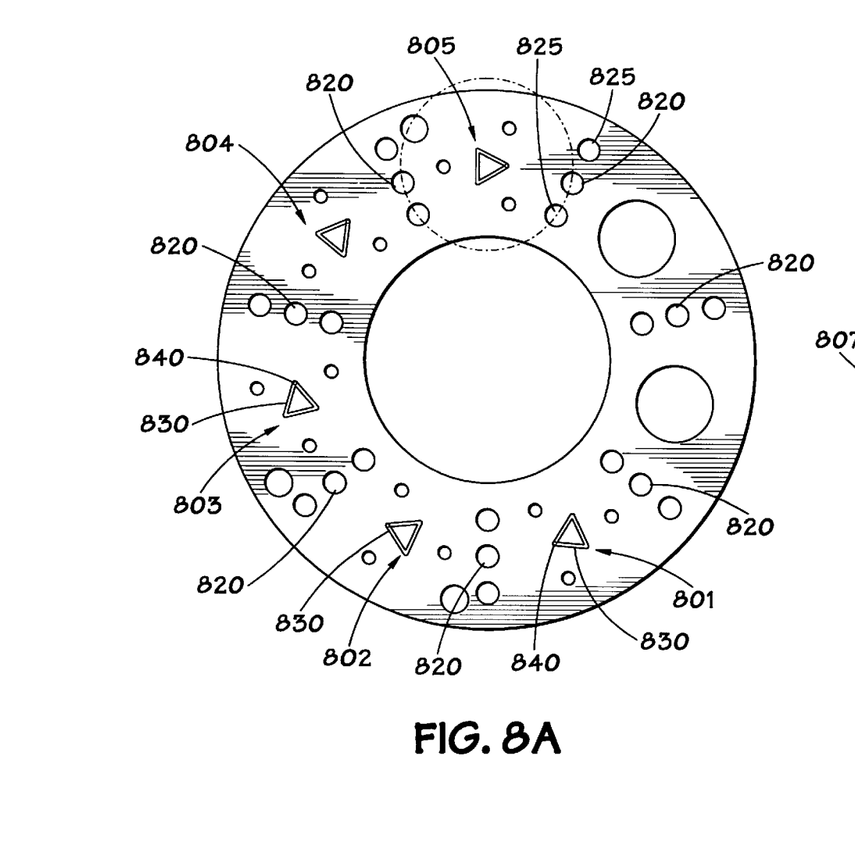
FIG. 8A is a top view of a lower piston plate for the multi-valve block of FIG. 6.
Figure 8B:
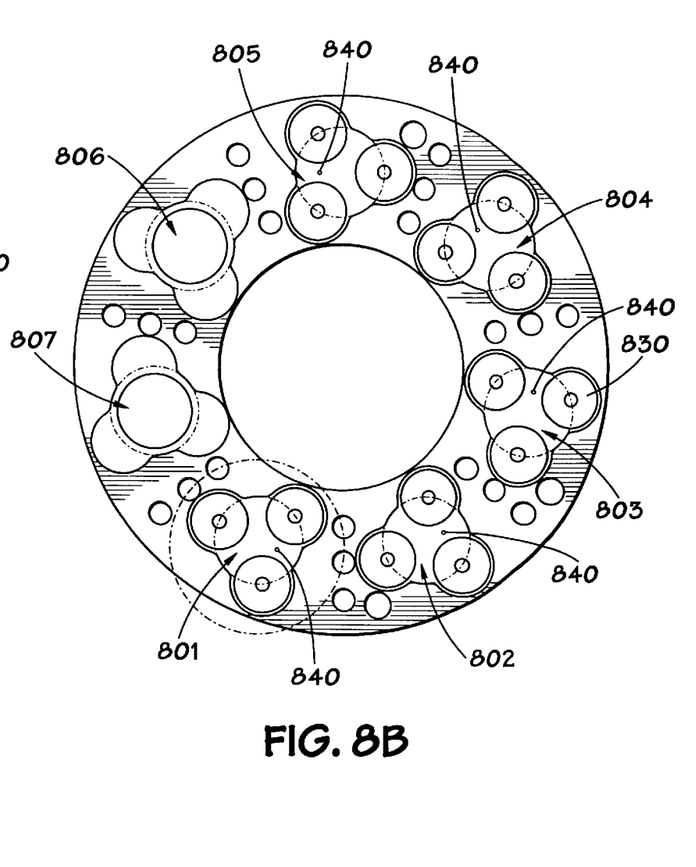
FIG. 8B is a bottom view of a lower piston plate for the multi-valve block of FIG. 6.

FIGS. 8A and 8B show the lower piston plate of FIG. 6. FIGS. 8A and 8B are the upper and lower views respectively of the lower piston plate. Referring to FIG. 8A, once again, locations 801–805 are provided for the five valves, in addition to an area for two sets of TCDs. Holes 820 and holes 825 accept tightening screws. Also shown are five triangular grooves 830 and accompanying holes 840 within each groove. Gas from the solenoids travels through the actuation holes 840 to the grooves 830. These grooves 830 provide a path for the actuation gas that elevates the short pistons. Because the valves of the illustrated embodiment have six ports, and thus three short pistons per valve, a triangular shape is convenient (but not necessary) to actuate all three short pistons simultaneously. Turning now to the bottom view of FIG. SB, locations 801–807 are shown. Also generally shown at 840 are holes connected to an actuator port through which gas exerts pressure. These holes 840 correspond to the grooves 830 of FIG. 8A. As can be seen, space 830 is provided for the base of long pistons 635.

Figure 9A:
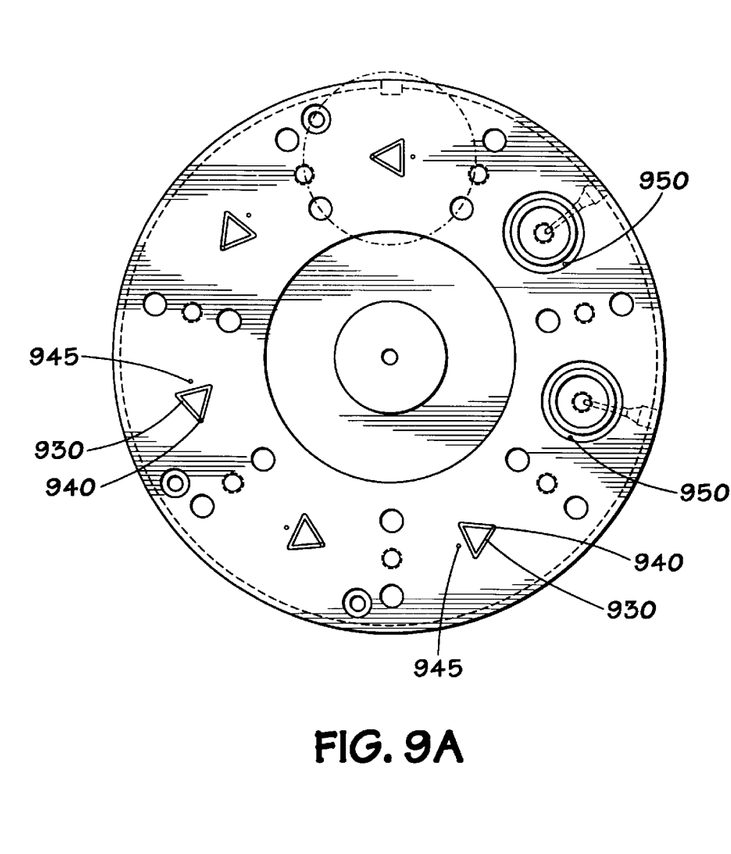
FIG. 9A is a top view of a base plate for the multi-valve block of FIG. 6.
Figure 9B:
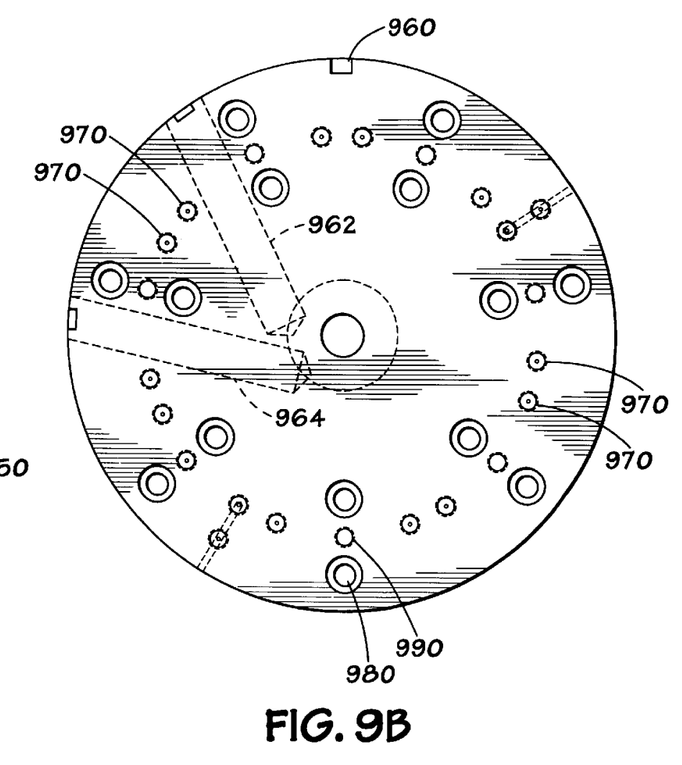
FIG. 9B is a bottom view of a base plate for the multi-valve block of FIG. 6.

FIGS. 9A and 9B show the top and bottom views respectively of the base plate. Referring to FIG. 9A, similar to FIG. 8A, a plurality of grooves 930 are shown, with each groove encompassing a hole 940 for actuator gas. In addition, actuator holes 945 traveling up to the lower piston plate are additionally shown. FIG. 9B illustrates the bottom view of the base plate. Illustrated are slot 960 and holes 970, 980, and 990. Slot 960 is present because it simplifies the removal of plates upon disassembly. In particular, after a valve has been assembled, the diaphragms tend to stick to a contact surface, and the slots provide an area where the plates can be easily grabbed onto. Hole 970 is a port A and B common line that connects to port A and B on solenoids via tubing. Holes 980 and 990 are screw holes. FIG. 9B also shows cross-drill lines 962 and 964 representing drilled areas for insertion of carrier and sample gas tubing. Holes at the entrance to each insertion area are also shown. The carrier and sample gas are quickly and reliably preheated in the insertion areas defined by cross-drill lines 962 and 964 from the warmth in the multi-valve block.

Figure 10A:
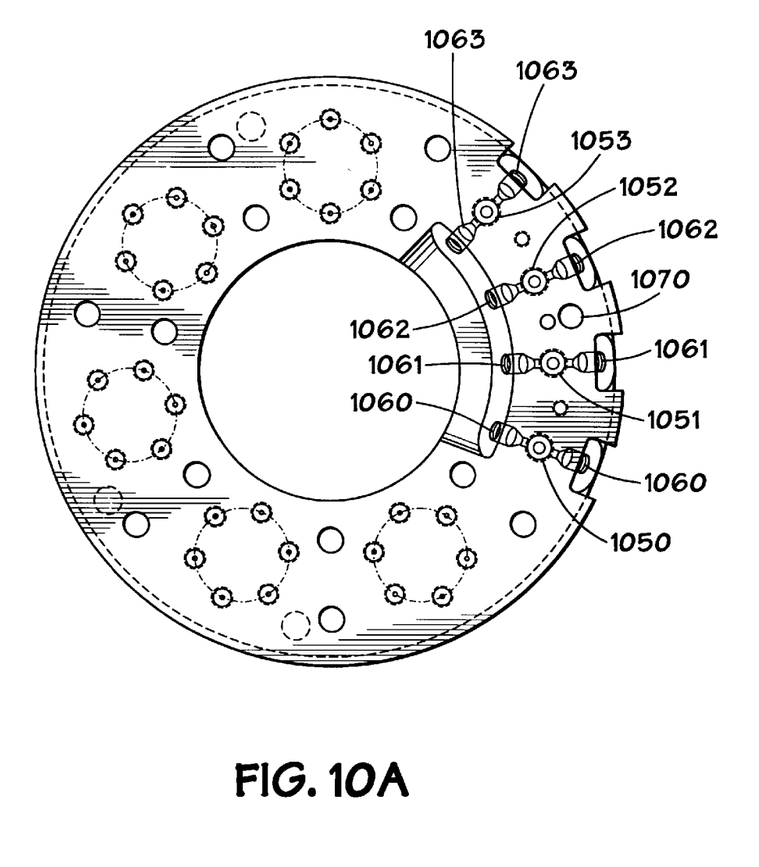
FIG. 10A is a top view of a primary plate for the multi-valve block of FIG. 6.
Figure 10B:
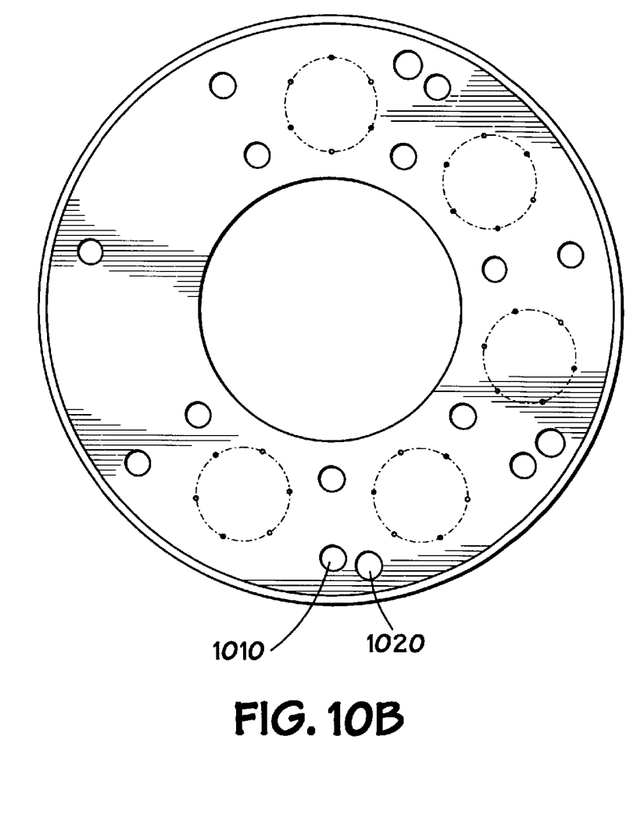
FIG. 10B is a bottom view of a primary plate for the multi-valve block of FIG. 6.

FIGS. 10A and 10B show the upper and lower view of a primary plate of FIG. 6. Referring now to FIG. 10A shown are TCD holes 1050–1053 and associated tubing holes 1060–1063. Also shown is a hole 1070 suitable for a RTD heat sensor. FIG. 10B shows a bottom view of the primary plate. Included are holes 1010 to accept screws and 1020 to accept dowel pins.

Figure 11:
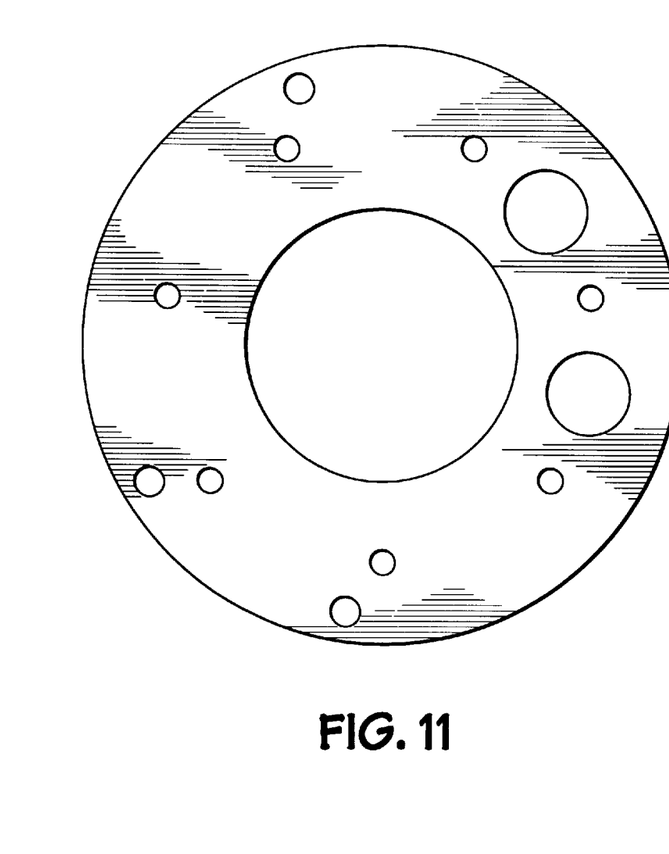
FIG. 11 is a sealing diaphragm for the multi-valve block of FIG. 6.
Figure 12:
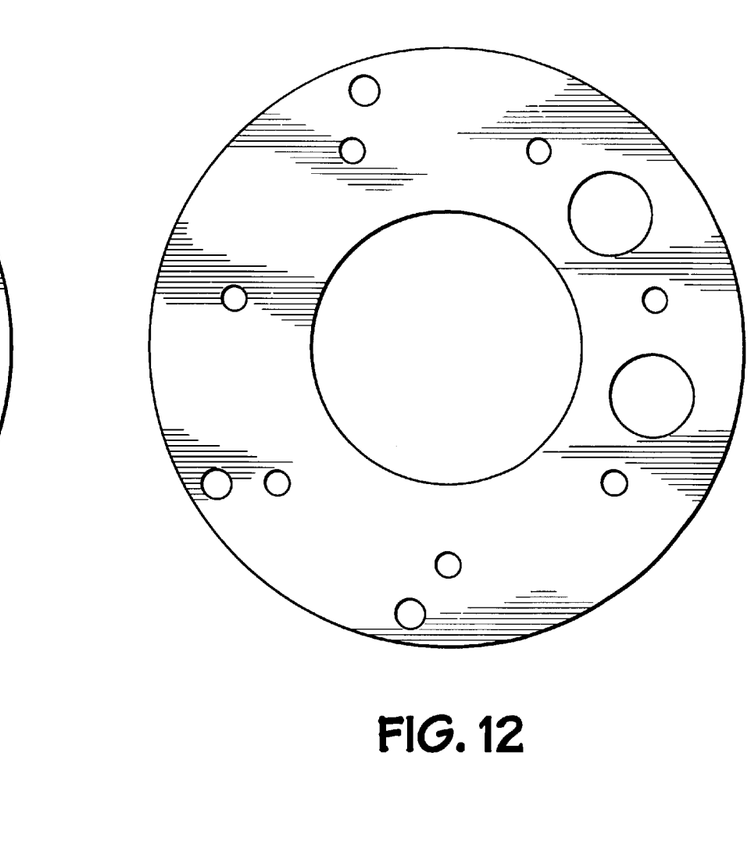
FIG. 12 is a cushion diaphragm for the multi-valve block of FIG. 6.
Figure 13A:
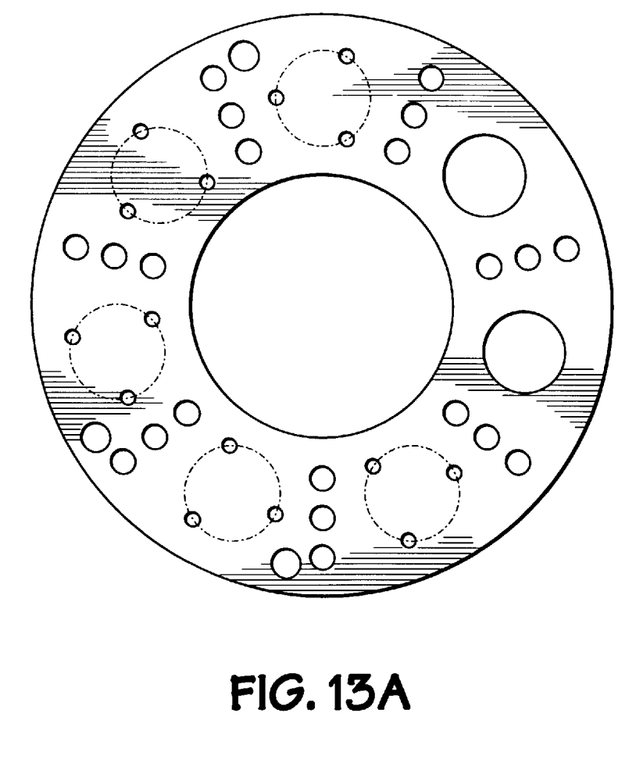
FIG. 13A is an upper actuator diaphragm for the multi-valve block of FIG. 6.
Figure 13B:
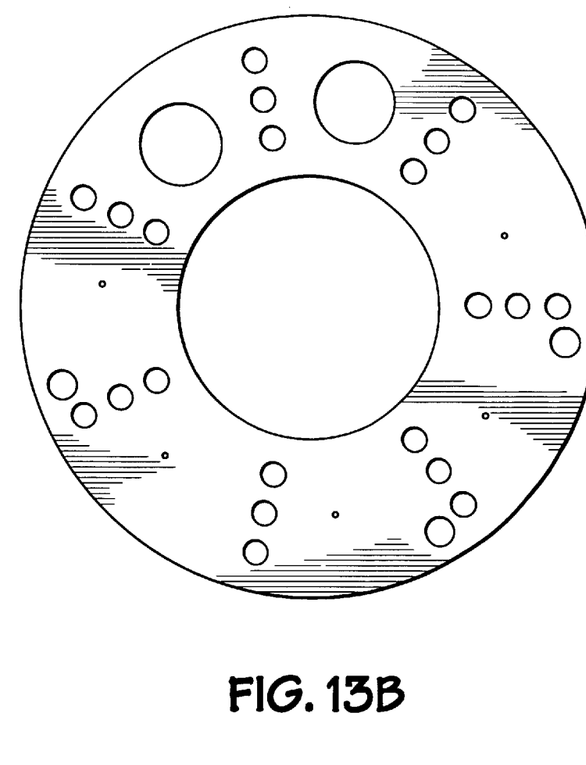
FIG. 13B is a lower actuator diaphragm for the multi-valve block of FIG. 6.

FIGS. 11–13 illustrate the diaphragms of FIG. 6. FIG. 11 shows the sealing diaphragm of FIG. 6. The sealing diaphragm is preferably made from 2 mil thick Kapton™ made by DuPont with a 0.5 mil teflon coating on each side. FIG. 12 shows the cushion diaphragm of FIG. 6. The cushion diaphragm is preferably about 0.002" thick and is made from Nomax paper by DuPont. FIGS. 13A and 13B illustrate upper and lower actuator diaphragms. Both actuator diaphragms are preferably made from 3 mil thick Kapon™ made by DuPont.

Figure 14:
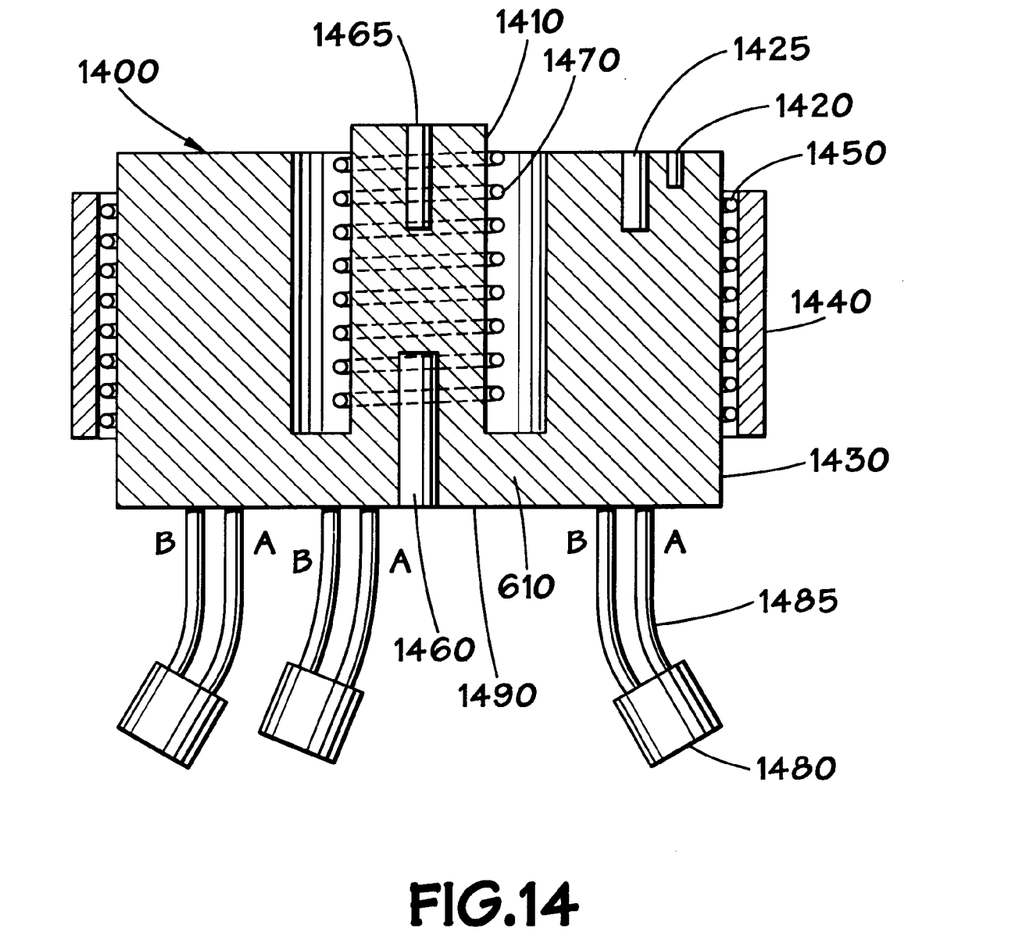
FIG. 14 is a cut-away view of a multi-valve assembly during operation.

FIG. 14 illustrates a multi-valve block 1400 including a spool 1410 with areas for a first RTD (Resistance Thermal Detector) 1420 and two TCD pairs 1425, an exterior surface 1430 to the multi-valve block 1400, a band heater 1440 outside of the exterior surface 1430, carrier gas preheat tubing 1450 located between the exterior surface 1430 and the band heater 1450, and a base plate 610 as part of the multi-valve block. Spool 1410 contains one or more cartridge heaters 1460 and a second RTD 1465. Referring back to FIG. 6, a hole or open area 605 is present in the middle of the multi-valve block. The open area 605 accommodates spool 1410 that protrudes from the base plate 610. Columns 1470 wraps around the spool 1410. Also shown are solinoids 1480 connected via tubing 1485 to the base plate at its lower end 1490. Band heater 1440 is an AC band heater of approximately 200 Watts power.

During operation, a gas sample flows through tubing or conduits 315 (not shown in FIG. 14) in the multi-valve block prior to flowing through the piping of the columns 1470. In contrast, the carrier gas flows through the carrier gas preheat tubing 1450 prior to flowing through columns 1470. The carrier gas preheat tubing may be located at different positions to heat the carrier gas to a predetermined temperature. The carrier gas preheat tubing may be just inside the band heater as shown in FIG. 14, or it may preferably occupy insertion areas in the multi-valve block, as explained in reference to FIG. 9. Thus, prior to being warmed by the spool, both the carrier gas and the gas sample are heated to approximately the temperature of the multi-valve block.

Thus, this arrangement provides for two heating zones. The area proximate to the spool 1410 defines a second heating zone. A first heating zone is defined by the temperature of the remainder of the multi-valve block. The first RTD located in the multi-valve block at 1420 measures the temperature of the first heating zone. The second RTD located at 1465 within the spool 1410 measures the temperature of the second heating zone. Two separate heating zones are important because the gas flowing through the columns 1470 should ideally be about 3–5° C. higher than the temperature at each TCD (the temperature of the first heating zone). In addition, the TCD's in the first heating zone should be kept to within about 0.1° C. of a predetermined temperature for accurate analysis. The temperature variation in the second heating zone should also be maintained within about a 0.1° C. tolerance. More heating zones may be added when desired to allow the analysis of the complex samples.

Figure 15:
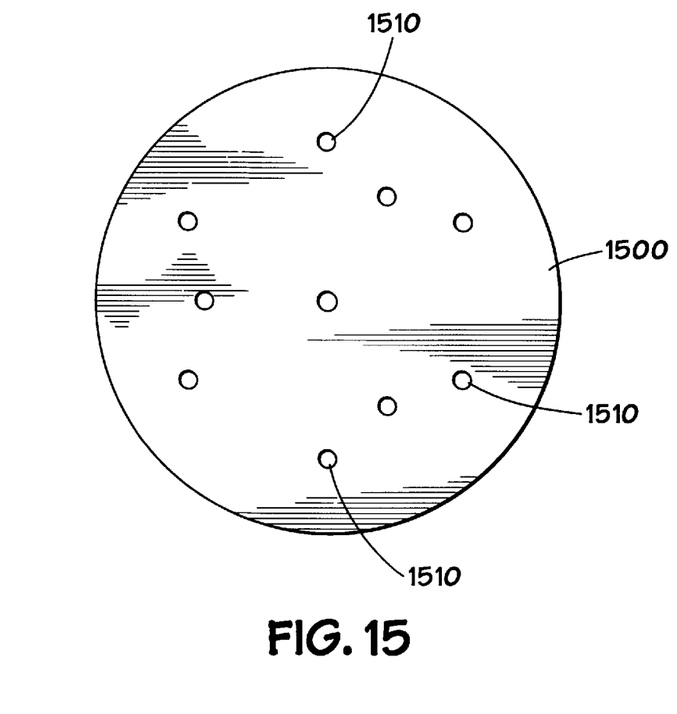
FIG. 15 is a top view of the bottom piece of insulation for a multi-valve assembly oven.

In order to stabilize the temperatures in heating zones, an "oven" is created from a thermal insulation material. This oven is essentially a cylindrical sleeve that surrounds the rest of the multi-valve device and keeps its temperature stable, except for the solenoids, which must be kept away from the heat inside the oven. Referring to FIG. 15, an illustrative bottom 1500 of this insulation cylinder or sleeve is shown. As can be seen, it contains a number of holes 1510, through which extend the tubing for the solenoids and the legs of the base stand.

Figure 16:
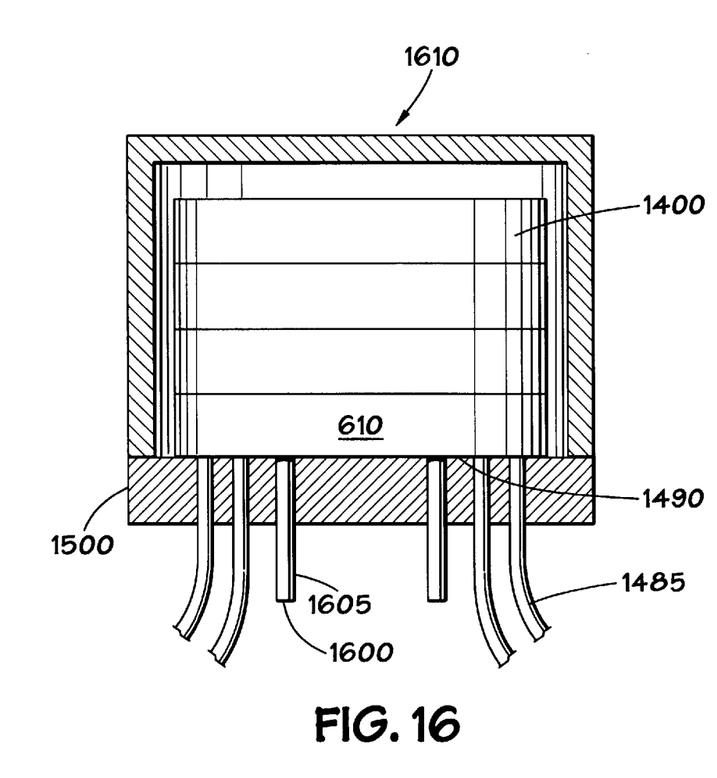
FIG. 16 is a cross-section view of an embodiment of the multi-valve assembly.

FIG. 16 illustrates the insulation 1610 for the "oven" including the bottom 1500 of the insulation cylinder. As part of them multi-valve block 1400, base plate 610 is adjacent to the bottom of the insulation cylinder 1500. Legs 1600 to create stand-off are made from Teflon™ 1605. Also shown is tubing 1485 that extends through the bottom piece 1500 to the lower surface 1490 of the multi-valve block 1400.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A multi-valve assembly, comprising:

an integrated unit including a plurality of plates and at least one diaphragm attached together to form multiple valves, each of said valves being independently actuatable and having a plurality of valve ports;

a number of said plates fonrning an open area in the body of each of said number of plates;

a spool occupying a portion of said open area, said plates defining at least a first heating zone and said spool defining at least a second heating zone.

wherein each of said first and said second heating zones include at least one temperature detector and wherein said first heating zone is maintained about a first predetermined temperature and said second heating zone is maintained at about a second predetermined temperature.

2. A multi-valve assembly. comprising:

an integrated unit including a plurality of plates and at least one diaphragm attached together to form multiple valves, each of said valves being independently actuatable and having a plurality of valve ports;

a number of said plates forming an open area in the body of each of said number of plates;

a spool occupying a portion of said open area, said plates defining at least a first heating zone and said spool defining at least a second heating zone, wherein said first heating zone is maintained by a band heater located approximately concentrically around at least one of said plates and said second heating zone is maintained by a second heater in said spool.

* * * * *